(12) United States Patent
Jannsen et al.

(10) Patent No.: US 6,798,216 B2
(45) Date of Patent: Sep. 28, 2004

(54) RESONANT MICROWAVE SENSOR

(75) Inventors: Bert Jannsen, Braunschweig (DE);
Arne Jacob, Braunschweig (DE)

(73) Assignee: Technische Universitat Braunschweig Carolb-Wilhelmina, Braunschweig (DE)

( * ) Notice: Subject to any disclaimer, the term of this patent is extended or adjusted under 35 U.S.C. 154(b) by 0 days.

(21) Appl. No.: 10/240,595

(22) PCT Filed: Jan. 10, 2002

(86) PCT No.: PCT/DE02/00054
§ 371 (c)(1),
(2), (4) Date: Oct. 3, 2002

(87) PCT Pub. No.: WO02/057762
PCT Pub. Date: Jul. 25, 2002

(65) Prior Publication Data
US 2003/0137313 A1 Jul. 24, 2003

(30) Foreign Application Priority Data
Jan. 20, 2001 (DE) .......................... 101 02 578

(51) Int. Cl.[7] .............................................. G01R 27/04
(52) U.S. Cl. ...................................... 324/646; 324/643
(58) Field of Search ................................ 324/632, 633, 324/636, 637, 644, 446, 643; 331/176; 356/136; 436/172

(56) References Cited

U.S. PATENT DOCUMENTS

| | | | |
|---|---|---|---|
| 3,946,308 A | | 3/1976 | Muira et al. |
| 4,755,743 A | * | 7/1988 | Jakkula .................. 324/632 |
| 5,334,941 A | * | 8/1994 | King ...................... 324/637 |
| 5,864,239 A | * | 1/1999 | Adams et al. ............ 324/636 |
| 6,031,436 A | * | 2/2000 | Fiedziuszko et al. ....... 333/202 |

FOREIGN PATENT DOCUMENTS

| | | |
|---|---|---|
| DE | 24 54 788 | 11/1974 |
| DE | 29 17 471 C2 | 4/1979 |
| DE | 39 15 477 C2 | 5/1989 |
| DE | 692 02 616 T2 | 3/1992 |
| DE | 693 15 208 T2 | 4/1993 |
| DE | 44 47 767 C2 | 9/1994 |
| DE | 196 50 112 C1 | 12/1996 |
| DE | 297 16 639 U1 | 9/1997 |
| EP | 0 908 718 A1 | 8/1998 |
| EP | 0 908 718 A1 | 4/1999 |

OTHER PUBLICATIONS

Derwent Publications Ltd., London , GB Patent Abstract XP-002215480 dated Apr. 6, 1984.
Patent Abstract RU 2084877-C1 dated Jul. 20, 1997.
PCT/DE 02/ 00054 European Search Report dated Oct. 14, 2002.
XP-010359354 Magazine Article dated Oct. 17-20, 1999, titled "Sensitivity of a Microwave Differential Technique for the Measurements of Contaminants in Gases".

* cited by examiner

*Primary Examiner*—N. Le
*Assistant Examiner*—Walter Benson
(74) *Attorney, Agent, or Firm*—Whitham, Curtis & Christofferson, P.C.

(57) ABSTRACT

An apparatus for determining the properties of a material, that is to be examined, by applying a swept-frequency high frequency signal and measuring a reflection factor of the resonance signal. The apparatus has a microwave supply conductor for feeding the high frequency signal, a sensor waveguide that is coupled to the microwave supply conductor, a helical conductor that is arranged inside the sensor waveguide, and an intermediate layer between a first end of the sensor waveguide and the helical conductor. Typically, the sensor waveguide is cylindrical and the helical conductor is supported centrally therein along the longitudinal axis of the sensor waveguide by a support that is part of the intermediate layer. A coupling layer is provided between the helical conductor and the material to be examined in the region of a second end face of the sensor waveguide.

14 Claims, 2 Drawing Sheets

RESONANT MICROWAVE SENSOR

The invention relates to a resonant microwave sensor for determining properties of a material, that is to be examined, by means of the high-frequency measurement of a reflection factor, having
- a microwave supply conductor for feeding the high-frequency signal, and
- a sensor waveguide that is coupled to the microwave supply conductor.

The measurement of material properties with the aid of microwave sensors by evaluating resonant frequencies and the quality of a resonance curve that is picked up by applying a swept-frequency high-frequency signal to the microwave sensor is sufficiently well known. In this case, the signal is coupled into the microwave sensor with a variable frequency, and the resonant frequency and, if appropriate, the quality, are determined.

Thus, German Utility Model 297 16 639 U1 describes a microwave stray-field sensor for measuring moisture and/or density, in the case of which a moist dielectric material is inserted into the resonator, and the density and humidity of the material are determined by shifting the resonant frequency. In order to avoid scattering losses that falsify the measurement result, it is proposed that the wavelength at the site of the generation of the resonance signal be substantially lower than in the free space of the resonator.

The resonator is constructed as a wire loop that is surrounded by a thin dielectric. In another embodiment, the resonator is formed from a circular dielectric ceramic body, the microwaves being coupled into the resonator via coaxial lines and capacitively active coupling pins.

These embodiments are likewise disclosed in EP 0 908 718 A1.

U.S. Pat. No. 3,946,308 discloses a microwave sensor for measuring moisture that has a dielectric resonator with a metallic conductor, a solid dielectric material, and an inlet antenna and an outlet antenna.

Furthermore, DE-A 24 54 788 A1 discloses a method and a device for determining the humidity of a gaseous medium. The basic method for measuring the humidity of a medium with the aid of the circuit quality of a resonance curve is to be gathered from this printed publication. With this method, a microwave oscillation of variable frequency, that is to say a swept-frequency signal, is coupled into the resonator and coupled out again separately therefrom. The amplitudes of the coupled-out oscillations are measured and recorded as a function of the frequency at constant amplitudes of the coupled-in oscillations.

In addition to these methods, in which the measurement information is obtained from the reflection at the material to be examined, methods are known in which the variation in the electromagnetic waves is evaluated during transmission through a material.

The problem of the known resonant microwave sensors that are based on the reflection method consists in scattering losses, broadbandedness and size. Moreover, the known microwave sensors cannot be integrated in optimum fashion in structures for in-situ measurement of characteristic material properties.

The object of the invention was therefore to create an improved generic resonant microwave sensor.

The object is achieved by means of a helical conductor that is arranged inside the sensor waveguide.

The use of the helical conductor as resonant metallic helix permits the construction of a compact sensor waveguide as resonator. Moreover, the resonant frequency of the microwave sensor can be set with the aid of the helical conductor.

The sensor waveguide as resonator is preferably a cylindrical tube, the microwave supply conductor being arranged, for example, as a coaxial hollow conductor at a first end face of the sensor waveguide. The second end face of the sensor waveguide is open, and so the material to be examined can penetrate into the resonator. There is a resultant variation in the dielectric properties of the filling in the sensor waveguide, and in the characteristic quantities of the resonator, that is to say the resonant frequency and quality are detuned. The properties of the material to be examined such as, for example, the relative humidity, can then be determined in a known way with the aid of these characteristic quantities.

The resonant frequency and quality of the sensor waveguide are calculated from the reflection factor R.

The helical conductor preferably extends in the longitudinal direction of the sensor waveguide.

The helical conductor is preferably held by a support and centered in the sensor waveguide.

For coupling purposes, an intermediate layer is advantageously provided between the first end face of the sensor waveguide and the helical conductor. The thickness of the intermediate layer determines the coupling factor. The quality of the sensor can be set with the aid of the intermediate layer. In order to enhance the measurement dynamics, the thickness of the intermediate layer should be selected so as to achieve the greatest possible coupling.

The resonant frequency of the microwave sensor is largely determined by the dimension of the helical conductor.

It is advantageous, furthermore, when an additional coupling layer is provided between the helical conductor and the material to be examined or a sensitive layer in the region of the second end face of the sensor waveguide. The thickness of the coupling layer determines the coupling of the helical conductor to the material to be examined, and thus the measurement sensitivity.

In the method for measuring properties of a material with the aid of a resonant microwave sensor described above, the frequency of the swept-frequency signal for exciting the microwave sensor should be lower than the cutoff frequency of the microwave sensor.

The length of the sensor waveguide should in this case be large enough to avoid emission to the outside and thus scattering losses.

The support and the intermediate layer are preferably designed in one piece.

It is particularly advantageous when the intermediate layer and/or the support consist of Teflon.

The invention is explained in more detail below with the aid of exemplary embodiments illustrated in the attached drawings, in which.

Figure 1:
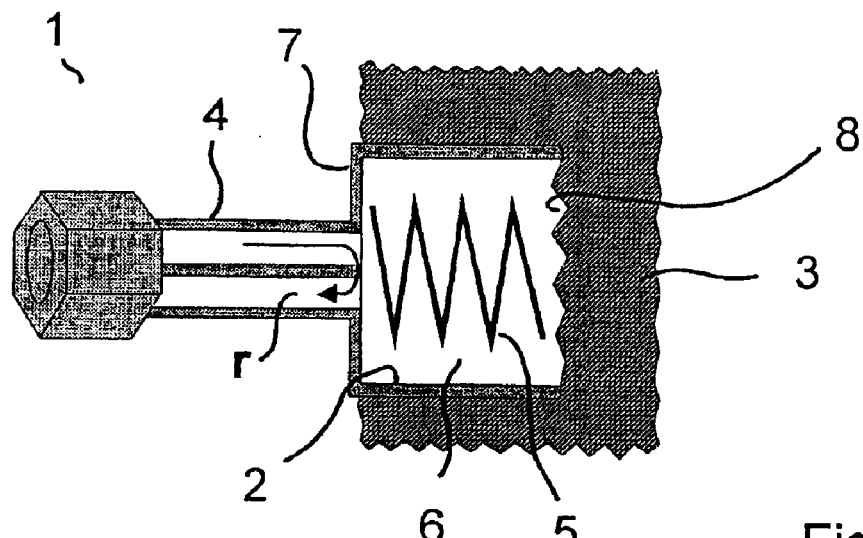
FIG. 1 shows a schematic of the microwave sensor according to the invention.

A resonant microwave sensor 1 according to the invention that is installed with a sensor waveguide 2 as resonator in the material 3 to be examined is to be gathered from FIG. 1. The microwave sensor 1 essentially comprises a microwave supply conductor 4 in the form of a coaxial hollow conductor, and the sensor waveguide 2 as resonator. Arranged in the sensor waveguide 2 is a helical conductor 5 that extends in the longitudinal direction of the sensor waveguide 2. The helical conductor 5 is a resonant conductive helix.

The sensor waveguide 2 is filled with a material 6 that is sensitive to the substance to be identified or to a property of the material 3 to be examined.

The microwave sensor 1 uses the microwave supply conductor 4 to apply a swept-frequency high-frequency signal in a frequency range adapted to the material 3 to be examined and to the microwave sensor 1, and the reflection factor r is measured in a known way.

The sensor waveguide 2 is coupled at a first end face 7 to the microwave supply conductor 4 and is open at the second end face 8. The substances to be identified can penetrate into the sensor waveguide 2 through the open second side face 8, for example by diffusion or by the gas phase. The dielectric properties of the sensitive filling of the sensor waveguide 2 are altered in the process, and the characteristic magnitudes of the resonator, that is to say the resonant frequency and quality, are detuned.

The deviations of the sensor waveguide 2 as resonator are fixed in the case of conventional circular waveguide resonators in essence by the cutoff frequencies $f_G$ of the eigenwaves of the circular waveguide (E waves or H waves) and the dielectric constant and permeability of the filling of the sensor waveguide 2. The length of the sensor waveguide 2 can be variable for the E waves. The radius of the sensor waveguide 2 is determined approximately by the equation $$r = \frac{2.405}{2\pi f_g \sqrt{\varepsilon\mu}} = \text{, } l \text{ variable}\cdot \quad E \text{ waves}$$

The radius of the sensor waveguide 2 is determined approximately for the H waves by the equation $$r = \frac{1.841\, l}{\pi\sqrt{(2f_g l)^2 \varepsilon\mu - 1}} \quad H \text{ waves}$$

The sensor waveguide 2 can be designed in a substantially more compact fashion by fitting the helical conductor 5 in the sensor waveguide 2. The resonant frequency of the resonator is determined in essence here by the dimensions, that is to say by the wire length, the radius and the pitch of the helical conductor 5.

Figure 2:
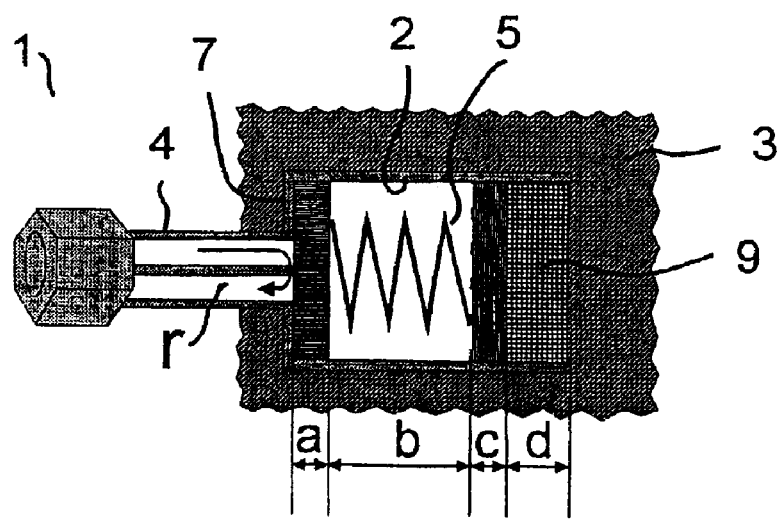
FIG. 2 shows a schematic of the microwave sensor according to the invention with intermediate layer and coupling layer.

FIG. 2 displays a further embodiment of the microwave sensor, in the case of which an intermediate layer a, preferably made from Teflon, is arranged between the first end face 7 of the sensor waveguide 2 and the helical conductor 5. This intermediate layer a serves the purpose of setting the spacing, and thus the coupling between the microwave supply conductor 4 and the helical conductor 5. The quality of the microwave sensor 1 can be set in essence with the aid of the intermediate layer a. The thickness of the intermediate layer should be selected so as to achieve as great a coupling as possible. The measurement dynamics can thereby be enhanced.

The helical conductor 5 can be held centrally in the sensor waveguide 2 on the intermediate layer a with the aid of a support. The support can be constructed in this case in an integral fashion with the intermediate layer a. The second layer b is determined in essence by the height of the helical conductor 5 and is instrumental in fixing the resonant frequency. Provided above the helical conductor 5 is a coupling layer c that determines the coupling of the helical conductor 5 to the sensitive material 9 for the purpose of identifying the substance to be measured, and therefore determines the measurement sensitivity.

The thickness c of the coupling layer and the thickness d of the sensitive material 9 must be selected large enough to provide emission, that is to say scattering, from the sensor waveguide 2.

Figure 3:
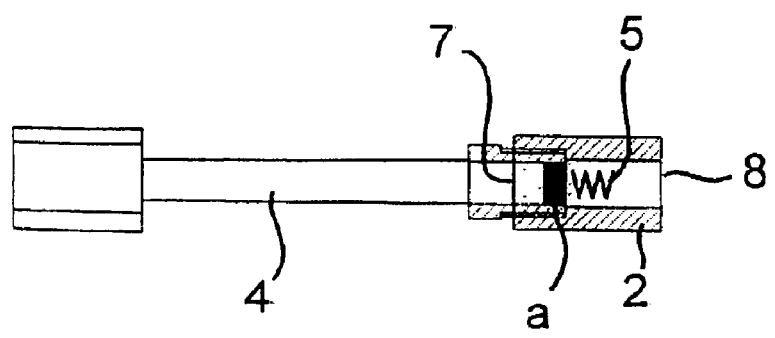
FIG. 3 shows a cross-sectional view of the microwave sensor according to the invention.

The design of the microwave sensor 1 is shown once again in cross section in FIG. 3. It is to be seen here that the microwave supply conductor 4 in the form of a flexible coaxial hollow conductor is screwed into the sensor waveguide 2, which is provided with a microwave plug. Also to be seen is the intermediate layer a with the support, integrally connected thereto, for the helical conductor 5, as well as the helical conductor 5.

The microwave sensor 1 is used in a frequency range of preferably from 1 to 6 GHz. The wire diameter of the helical conductor 5 is preferably approximately 0.2 mm, and the ratio of the diameter to the pitch of the helical conductor 5 is in the region of approximately 75.

Figure 4:
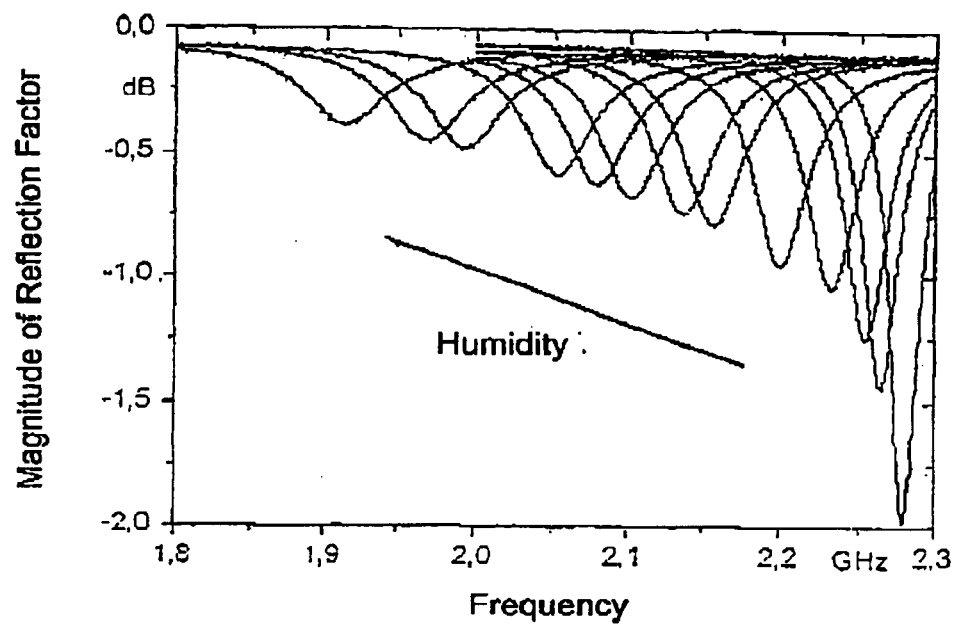
FIG. 4 shows a diagram of the magnitude of the reflection factor for various measured relative air humidities.

FIG. 4 shows a diagram of the magnitude of the reflection factor for various relative air humidities as a function of frequency. It becomes clear that the resonant frequencies shift as a function of the relative air humidity, a reduction in the resonant frequency resulting given an increase in the relative air humidity. It is to be seen, furthermore, that the quality of the resonator decreases with rising relative air humidity.

Figure 5:
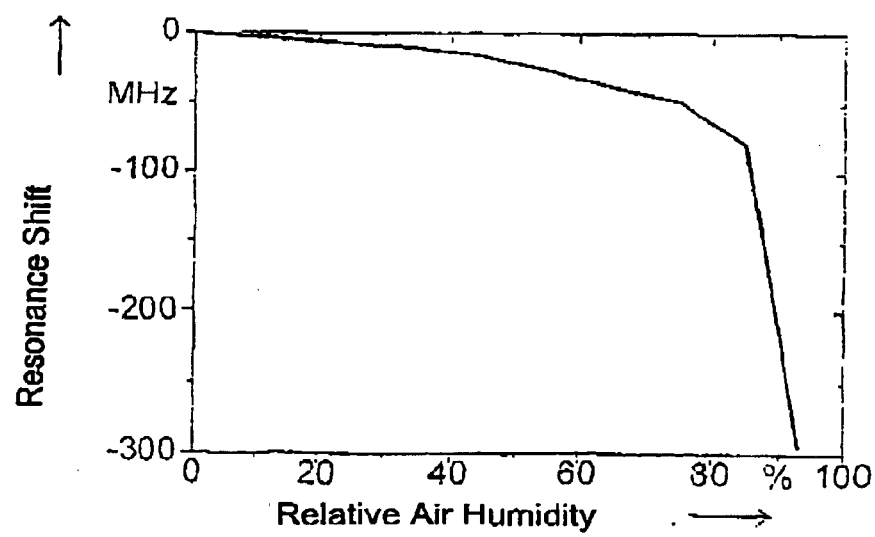
FIG. 5 shows a diagram of the resonance shift as a function of the relative humidity as a calibration curve for the microwave sensor.

The measured reflection factors can be used to determine a calibration curve for the microwave sensor that is plotted in FIG. 5 as a resonance shift as a function of the relative air humidity. A direct conclusion on a relative air humidity can be reached directly from the resonant frequency by using the calibration curve in conjunction with subsequent measurements.

The use of the microwave sensor 1 is not limited to the application as moisture sensor. It can equally be used to measure material properties that lead to a change in the dielectric properties of the sensitive material in the sensor waveguide 2.

What is claimed is:

1. A resonant microwave sensor for determining properties of a material, that is to be examined, by means of measurement of a reflection factor of a high frequency signal, having
   a microwave supply conductor for feeding the high-frequency signal,
   a sensor waveguide that is coupled to the microwave supply conductor, and
   a helical conductor, the helical conductor being arranged inside the sensor waveguide,
   characterized by
   an intermediate layer between a first end face of the sensor waveguide and helical conductor.

2. The resonant microwave sensor as claimed in claim 1, characterized in that the sensor waveguide is a cylindrical tube, the microwave supply conductor is arranged at the first end face of the sensor waveguide, and a second end face at an end of the sensor waveguide opposite to the first end face is open.

3. The resonant microwave sensor as claimed in claim 2, characterized in that the helical conductor extends in the longitudinal direction of the sensor waveguide.

4. The resonant microwave sensor as claimed in claim 3, characterized by a coupling layer between the helical conductor and the material to be examined, which material is located in the region of the second end face of the sensor waveguide.

5. The resonant microwave sensor as claimed in claim 2, characterized by a coupling layer between the helical conductor and the material to be examined, which material is located in the region of the second end face of the sensor waveguide.

6. The resonant microwave sensor as claimed in claim 1, characterized by a support for the helical conductor for centering the helical conductor in the sensor waveguide.

7. The resonant microwave sensor as claimed in claim 6, characterized in that the support and the intermediate layer are in one piece.

8. The resonant microwave sensor as claimed in claim 7, characterized in that the intermediate layer and/or the support consist of Teflon.

9. The resonant microwave sensor as claimed in claim 7, characterized by a coupling layer between the helical conductor and the material to be examined, which material is located in the region of the second end face of the sensor waveguide.

10. The resonant microwave sensor as claimed in claim 6, characterized in that the intermediate layer and/or the support consist of Teflon.

11. The resonant microwave sensor as claimed in claim 10, characterized by a coupling layer between the helical conductor and the material to be examined, which material is located in the region of the second end face of the sensor waveguide.

12. The resonant microwave sensor as claimed in claim 6, characterized by a coupling layer between the helical conductor and the material to be examined, which material is located in the region of a second end face of the sensor waveguide, being at an end of the sensor waveguide opposite to the first end face.

13. A method for measuring properties of a material with the aid of a resonant microwave sensor as claimed in claim 1, the microwave sensor being excited with the aid of swept-frequency high-frequency signals and the reflection factor being determined as a measured variable for determining properties of the material to be examined, characterized in that the frequency of the swept-frequency signal for exciting the microwave sensor is lower than the cutoff frequency of the microwave sensor.

14. The resonant microwave sensor as claimed in claim 1, characterized in that the intermediate layer consists of Teflon.

* * * * *